(12) United States Patent
Vogt et al.

(10) Patent No.: US 9,073,081 B2
(45) Date of Patent: Jul. 7, 2015

(54) DISPENSING DEVICE FOR PASTY MATERIALS

(75) Inventors: Sebastian Vogt, Erfurt (DE); Hubert Büchner, Nürnberg (DE)

(73) Assignee: Heraeus Medical GmbH, Wehrheim (DE)

( * ) Notice: Subject to any disclaimer, the term of this patent is extended or adjusted under 35 U.S.C. 154(b) by 186 days.

(21) Appl. No.: 13/096,062

(22) Filed: Apr. 28, 2011

(65) Prior Publication Data
US 2011/0272437 A1   Nov. 10, 2011

(30) Foreign Application Priority Data
May 4, 2010   (DE) .......................... 10 2010 019 224

(51) Int. Cl.
*B05C 17/015* (2006.01)
*A61B 17/88* (2006.01)
(Continued)

(52) U.S. Cl.
CPC ........... *B05C 17/015* (2013.01); *A61B 17/8822* (2013.01); *A61B 17/8825* (2013.01); *A61B 17/8827* (2013.01); *B05C 17/00553* (2013.01);
(Continued)

(58) Field of Classification Search
CPC ............................... B05C 17/015; F16N 11/10
USPC ......... 222/389, 399, 391, 387, 325, 326, 327, 222/386, 394, 83, 83.5, 88, 81, 5, 397, 188, 222/484, 94, 160, 153.11, 478; 124/74
See application file for complete search history.

(56) References Cited

U.S. PATENT DOCUMENTS

| 1,092,433 A | 4/1914 | Cox |
| 1,308,091 A * | 7/1919 | Maurer, Jr. et al. ............. 222/61 |

(Continued)

FOREIGN PATENT DOCUMENTS

| AU | 653201 | 9/1994 |
| CH | 669164 | 2/1989 |

(Continued)

OTHER PUBLICATIONS

European Search Report Dated September 13, 2011 for EP 11 00 3139 corresponding to present application.
(Continued)

*Primary Examiner* — Kevin P Shaver
*Assistant Examiner* — Michael J Melaragno
(74) *Attorney, Agent, or Firm* — Norris McLaughlin & Marcus, P.A.

(57) ABSTRACT

A dispensing device for cartridges having a connection for supplying a pressurized gas, a base body, in which at least one passage and/or channel extends through which the pressurized gas can be guided to a first cartridge connector for connecting a cartridge. The first cartridge connector has a first opening towards the passage and/or the front channel such that a cartridge content can be expelled from the cartridge through application of the pressurized gas to a cartridge when the cartridge is arranged in the cartridge connector, wherein a second cartridge connector having a larger cross-section and a second opening is arranged at a front edge of the first cartridge connector The second cartridge connector is suitable for connecting a larger cartridge, and wherein the second opening of the second cartridge connector is sufficiently large to allow a cartridge to be connected to the first cartridge connector proceeding through the second opening.

19 Claims, 5 Drawing Sheets

(51) Int. Cl.
*B05C 17/005* (2006.01)
*A61B 17/00* (2006.01)

(52) U.S. Cl.
CPC ... *B05C 17/00559* (2013.01); *A61B 2017/0023* (2013.01)

(56) References Cited

U.S. PATENT DOCUMENTS

| | | | |
|---|---|---|---|
| 1,920,165 A | 8/1933 | Andvig | |
| 2,125,245 A | 7/1938 | McCray | |
| 2,446,501 A | 8/1948 | Weber | |
| 2,694,506 A * | 11/1954 | Knapp | 222/5 |
| 2,818,899 A | 1/1958 | De Back | |
| 2,973,885 A | 3/1961 | Ferguson | |
| 3,116,856 A | 1/1964 | Prussin et al. | |
| 3,136,456 A * | 6/1964 | Sherbondy | 222/327 |
| 3,215,298 A | 11/1965 | Shaffer | |
| 3,282,473 A * | 11/1966 | Moore | 222/327 |
| 3,570,719 A | 3/1971 | Schiff | |
| 3,603,487 A * | 9/1971 | Cook | 222/389 |
| 3,752,368 A * | 8/1973 | Robertson | 222/327 |
| 3,768,472 A * | 10/1973 | Hodosh et al. | 604/143 |
| 3,813,012 A * | 5/1974 | Laird | 222/326 |
| 3,834,433 A | 9/1974 | Thompson | |
| 3,938,709 A | 2/1976 | Collar | |
| 3,983,947 A * | 10/1976 | Wills et al. | 173/169 |
| 4,068,830 A | 1/1978 | Gray | |
| 4,174,868 A * | 11/1979 | De Nardo | 406/76 |
| 4,318,403 A | 3/1982 | Sneider | |
| 4,386,717 A * | 6/1983 | Koob | 222/94 |
| 4,432,469 A | 2/1984 | Eble et al. | |
| 4,441,629 A * | 4/1984 | Mackal | 222/324 |
| 4,634,027 A * | 1/1987 | Kanarvogel | 222/380 |
| 4,676,410 A * | 6/1987 | von Flue | 222/327 |
| 4,690,306 A | 9/1987 | Staheli | |
| 4,846,373 A | 7/1989 | Penn et al. | |
| 4,848,598 A | 7/1989 | McKinney | |
| 4,871,088 A | 10/1989 | Cox | |
| 4,925,061 A | 5/1990 | Jeromson, Jr. et al. | |
| 4,967,797 A * | 11/1990 | Manska | 137/625.47 |
| 4,981,241 A | 1/1991 | Keller | |
| 4,989,758 A | 2/1991 | Keller | |
| 5,027,981 A | 7/1991 | Magister | |
| 5,072,862 A | 12/1991 | Keller | |
| 5,080,262 A | 1/1992 | Herold et al. | |
| 5,137,182 A | 8/1992 | Keller | |
| 5,156,421 A * | 10/1992 | Chauvel | 285/40 |
| 5,301,631 A | 4/1994 | Vining | |
| 5,301,842 A | 4/1994 | Ritter | |
| 5,361,946 A * | 11/1994 | Ginther et al. | 222/175 |
| 5,441,175 A | 8/1995 | Jacobsen et al. | |
| 5,443,182 A | 8/1995 | Tanaka et al. | |
| 5,477,987 A | 12/1995 | Keller | |
| 5,498,078 A | 3/1996 | Keller | |
| 5,514,135 A * | 5/1996 | Earle | 606/93 |
| 5,566,860 A | 10/1996 | Schiltz et al. | |
| 5,667,102 A | 9/1997 | Keller | |
| 5,890,628 A | 4/1999 | Simpson et al. | |
| 5,893,486 A | 4/1999 | Wasmire | |
| 5,894,869 A * | 4/1999 | Mussack | 141/19 |
| 5,944,226 A | 8/1999 | Schiltz et al. | |
| 5,968,018 A | 10/1999 | Freeman et al. | |
| 6,029,857 A | 2/2000 | Keller | |
| 6,077,138 A | 6/2000 | Schulze | |
| 6,223,941 B1 * | 5/2001 | Nealey | 222/82 |
| 6,296,149 B1 | 10/2001 | Long | |
| 6,311,871 B1 | 11/2001 | Binder | |
| 6,547,101 B1 | 4/2003 | Sogaro | |
| 6,783,509 B1 | 8/2004 | Landau et al. | |
| 6,935,541 B1 * | 8/2005 | Campbell et al. | 222/380 |
| 7,163,130 B2 * | 1/2007 | Lafond | 222/326 |
| 7,185,792 B2 * | 3/2007 | Gibbons et al. | 222/387 |
| 7,188,753 B2 * | 3/2007 | Campbell | 222/389 |
| 7,481,333 B2 | 1/2009 | Goldberg et al. | |
| 7,530,808 B2 | 5/2009 | Cao et al. | |
| 7,637,398 B2 * | 12/2009 | Sung | 222/389 |
| 7,677,418 B2 * | 3/2010 | Henniges et al. | 222/327 |
| 7,752,974 B2 | 7/2010 | Wenaas et al. | |
| 7,845,517 B2 * | 12/2010 | Py et al. | 222/83.5 |
| 7,963,937 B2 | 6/2011 | Pauser et al. | |
| 8,016,161 B2 | 9/2011 | Pierson et al. | |
| 8,028,858 B2 * | 10/2011 | Hollars | 222/5 |
| 8,177,099 B2 | 5/2012 | Suchan et al. | |
| 8,292,619 B2 | 10/2012 | Peuker et al. | |
| 8,328,553 B2 | 12/2012 | Broyles et al. | |
| 2001/0008968 A1 | 7/2001 | Overes et al. | |
| 2002/0052579 A1 | 5/2002 | Sogaro | |
| 2002/0146662 A1 | 10/2002 | Radl et al. | |
| 2002/0188250 A1 | 12/2002 | Landau et al. | |
| 2003/0179648 A1 | 9/2003 | Heusser et al. | |
| 2004/0074927 A1 * | 4/2004 | Lafond | 222/327 |
| 2004/0104249 A1 | 6/2004 | Horth et al. | |
| 2004/0216591 A1 | 11/2004 | Assadi et al. | |
| 2005/0150903 A1 | 7/2005 | Py et al. | |
| 2005/0150916 A1 | 7/2005 | De Laforcade | |
| 2005/0230433 A1 * | 10/2005 | Campbell | 222/389 |
| 2005/0241703 A1 * | 11/2005 | Takacs | 137/625.46 |
| 2005/0247740 A1 * | 11/2005 | Puzio | 222/389 |
| 2005/0269368 A1 * | 12/2005 | Proulx | 222/326 |
| 2006/0208000 A1 * | 9/2006 | Murray et al. | 222/135 |
| 2007/0051750 A1 | 3/2007 | Suchan et al. | |
| 2007/0164047 A1 | 7/2007 | Reidt et al. | |
| 2007/0175921 A1 | 8/2007 | Keller | |
| 2008/0086079 A1 | 4/2008 | Williamson et al. | |
| 2008/0210708 A1 | 9/2008 | Yesmes | |
| 2008/0247262 A1 * | 10/2008 | Henniges et al. | 366/47 |
| 2008/0287880 A1 | 11/2008 | Keller | |
| 2008/0304355 A1 | 12/2008 | Sattig et al. | |
| 2008/0314929 A1 | 12/2008 | Keller | |
| 2009/0057338 A1 | 3/2009 | Knee et al. | |
| 2009/0062808 A1 | 3/2009 | Wolf, II | |
| 2009/0065532 A1 * | 3/2009 | Lafond | 222/389 |
| 2009/0071459 A1 | 3/2009 | Wenaas et al. | |
| 2009/0105144 A1 | 4/2009 | Vogt et al. | |
| 2009/0105366 A1 | 4/2009 | Vogt et al. | |
| 2009/0127289 A1 | 5/2009 | Keller | |
| 2010/0200618 A1 | 8/2010 | Dubach | |
| 2010/0213217 A1 * | 8/2010 | Strong et al. | 222/327 |
| 2010/0319796 A1 * | 12/2010 | Whitaker | 137/625.46 |
| 2011/0272436 A1 | 11/2011 | Vogt et al. | |
| 2011/0272438 A1 | 11/2011 | Vogt et al. | |
| 2011/0311730 A1 * | 12/2011 | Atsebha et al. | 427/421.1 |
| 2012/0104050 A1 | 5/2012 | Mossle | 222/409 |
| 2013/0152855 A1 * | 6/2013 | Hartman et al. | 118/300 |

FOREIGN PATENT DOCUMENTS

| | | |
|---|---|---|
| CN | 101203327 A | 6/2008 |
| DE | 3440893 | 5/1986 |
| DE | 3530212 C1 | 10/1986 |
| DE | 91 02 635 U1 | 5/1991 |
| DE | 2017292 | 10/1997 |
| DE | 297 09 383 U1 | 10/1998 |
| DE | 20107507 U1 | 3/2002 |
| DE | 202005010206 | 9/2005 |
| DE | 20 2006 014087 U1 | 12/2006 |
| DE | 102005041961 A1 | 3/2007 |
| DE | 102006001056 A1 | 7/2007 |
| DE | 202006015457 U1 | 2/2008 |
| DE | 20 2008 009692 U1 | 10/2008 |
| DE | 102007044983 A1 | 4/2009 |
| DE | 102007052116 A1 | 4/2009 |
| DE | 102007050762 A1 | 5/2009 |
| DE | 102008030312 A1 | 1/2010 |
| EP | 0028032 A1 | 5/1981 |
| EP | 0169533 A2 | 1/1986 |
| EP | 0213073 A1 | 3/1987 |
| EP | 0236129 A2 | 9/1987 |
| EP | 0261466 A1 | 3/1988 |
| EP | 0289882 A1 | 11/1988 |
| EP | 0294672 A1 | 12/1988 |
| EP | 0431347 A1 | 6/1991 |
| EP | 0607102 A1 | 7/1994 |

(56) References Cited

FOREIGN PATENT DOCUMENTS

| | | | |
|---|---|---|---|
| EP | 0664153 | A1 | 7/1995 |
| EP | 0693437 | A1 | 1/1996 |
| EP | 0787535 | A1 | 8/1997 |
| EP | 1118313 | A1 | 7/2001 |
| EP | 15441223 | A1 | 6/2005 |
| EP | 2008707 | A1 | 12/2008 |
| FR | 650 157 | A | 1/1929 |
| GB | 1188516 | | 4/1970 |
| GB | 2195713 | A | 4/1988 |
| JP | 2003341749 | A | 12/2003 |
| JP | 2005289470 | A | 10/2005 |
| JP | 2009529377 | A | 8/2009 |
| JP | 2009 291234 | A | 12/2009 |
| WO | 2006005206 | | 1/2006 |
| WO | 2008100130 | A2 | 8/2008 |
| WO | 2008109439 | | 9/2008 |
| WO | 2009036962 | A2 | 3/2009 |
| WO | 2009/061884 | A1 | 5/2009 |
| WO | 2010006455 | | 1/2010 |

OTHER PUBLICATIONS

European Search Report Dated September 15, 2011, corresponding to U.S. Appl. No. 13/096,105.

"Australian Search Report dated Jul. 28, 2012 for AU Application No. 2011201857 corresponding to related U.S. Appl. No. 13/096,260."

Canadian Intellectual Property Office, Office Action dated Aug. 1, 2012.

Australian Search Report for related AU 2011202037, mailed Aug. 16, 2012.

Chinese Office Action for co-pending U.S. Appl. No. 13/096,156 for related Chinese Application No. 201110113264.4 dated Feb. 4, 2013.

Chinese Office Action for co-pending U.S. Appl. No. 13/096,105 for related Chinese Application No. 201110114689.3 dated Dec. 9, 2013 with English-Language Translation.

Japanese Office Action for corresponding JP Application No. 2011-103862 dated Jul. 29, 2013 with English-Language Translation.

Chinese Office Action for co-pending U.S. Appl. No. 13/096,233 for related Chinese Application No. 201110113261.0 dated Nov. 21, 2013 with English-Language Translation.

Non-Final Rejection from related U.S. Appl. No. 13/096,260, mailed Jul. 10, 2013.

Notice of Allowance from related U.S. Appl. No. 13/096,233, mailed Aug. 1, 2013.

Notice of Allowance from related U.S. Appl. No. 13/096,156, mailed Aug. 26, 2013.

Final Rejection from related U.S. Appl. No. 13/096,105, mailed Aug. 28, 2013.

Non-Final Rejection from related U.S. Appl. No. 13/096,260, mailed Jun. 5, 2014.

* cited by examiner

DISPENSING DEVICE FOR PASTY MATERIALS

The present invention relates to a dispensing device for cartridges comprising a connection for supplying a pressurised gas, a base body, in which at least one passage and/or channel extends through which the pressurised gas can be guided to a first cartridge connector for connecting a cartridge, whereby the first cartridge connector comprises a first opening towards the passage and/or the front channel such that a cartridge content can be expelled from the cartridge through application of the pressurised gas to a cartridge that is arranged in the cartridge connector.

Accordingly, the subject matter of the invention is a dispensing device for squeezing out flow-able materials from cartridges. The dispensing device is designed, in particular, for dispensing bone cements. It has been known for decades to squeeze out cartridges through compressed gases.

BACKGROUND OF THE INVENTION

U.S. Pat. No. 2,818,899 proposes a sealant gun that contains a gas cartridge in its grip part. Once the cartridge is opened, the compressed gas of the gas cartridge presses a plunger within a cartridge in the direction of the cartridge head. The flow of the pasty mass is controlled by a central rod that extends through the cartridge and can close the outlet opening of the cartridge.

U.S. Pat. No. 3,938,709 (1976) describes a dispensing device in which gas pressure is used to squeeze out a tube that is situated inside the hollow gun body. In this context, the gas flow is attained through a simple pin valve having a spring that can be actuated through a manual lever. A device for discharge of the gas was not provided. This means that the gun continues to press on the material due to the existing residual pressure despite the gas feed being interrupted.

EP 0 169 533 A2 (1985) discloses an injection device for viscous substances. In this device, the squeezing process does not continue after the supply of compressed gas is interrupted, because an injection control valve that interrupts the flow of viscous substance is situated at the outlet opening. What is interesting in this context is that the valve of the trigger grip can be used to control both the supply of gas and, simultaneously, the exit of the viscous substance. The injection control valve closes when there is no application of compressed gas.

A similar system is described in U.S. Pat. No. 4,925,061. However, in this system the injection control valve is actuated through a rod that is connected to the trigger grip.

A gun for squeezing out bone cement is disclosed in EP 1 118 313 A1. The propulsion is effected through a gas cartridge in this case also. What is essential is that this very complex system includes a rod that serves the purpose to expel the residual amount of cement contained in the dispensing tube. This elegant technical solution is very well-suited for conventional poly-methyl-methacrylate bone cements. However, said gun cannot be used for cartridge systems for mixing multiple components with a static mixer. Moreover, the manufacture of said gun is very elaborate.

US 2004/0074927 A1 describes an applicator gun which discloses essentially the same features as U.S. Pat. No. 4,925,061.

Printed publications US 2005/0230433 A1, US 2005/0247740 A1, and U.S. Pat. No. 6,935,541 B1 propose basically the same technical solution that is known already from EP 0 169 533 A2.

WO 2008/109439 A1 discloses a compressed gas-operated dispensing device that uses a hydraulic medium onto which the compressed gas presses.

It should be noted that the dispensing devices known to date, which are propelled by gas cartridges and have a complex mechanical structure, are suitable for manufacture as single-use articles only to a limited extent or not at all. Especially the valves proposed thus far are very expensive and thus make the use of the dispensing devices as single-use articles questionable. Moreover, the proposed technical solutions are difficult to implement in the form of plastic injection moulding parts.

SUMMARY OF THE INVENTION

Accordingly, the invention is to provide a simple dispensing device for flowable materials that is easy to handle and inexpensive to manufacture. In the scope of the present invention, flowable materials are understood to mean liquid, viscous, even highly viscous, tenacious materials that are made to flow only through the application of pressure. The flowable materials are to be dispensed through compressed gas, which, for example, is taken from an insertable gas cartridge or compressed gas cartridge that is situated in the device. Said device is to consist of as few parts as possible that can be made through inexpensive injection moulding using conventional plastic materials. For this purpose, it is necessary to develop a straightforward, simple valve system that allows the gas flow to be controlled for an application time of the dispensing device of maximally 5 minutes. The dispensing device should be mountable through few manual steps and should be manufactured without difficulty in large numbers. It is also desirable for the dispensing device to be suitable as a disposable article for single use. It would also be advantageous if the user were able to detect the operating status of the dispensing device on the outside.

The invention is based on the object to allow at least two cartridges with different diameters to be connected. This would allow pasty materials from different cartridge systems to be squeezed out through just one dispensing device. This feature would entail economic advantages with regard to the amortisation of the dispensing device.

Said object is met in that a second cartridge connector having a larger cross-section and a second opening is arranged at the front edge of the first cartridge connector, whereby the second cartridge connector is suitable for connecting a larger cartridge, and whereby the second opening of the second cartridge connector is sufficiently large to allow a cartridge to be connected to the first cartridge connector proceeding through the second opening.

In this context, the invention can provide the cartridge connectors to be cylindrical hollow bodies having one closed side, whereby the closed side of the second cartridge connector comprises the second opening and the closed side of the first cartridge connector comprises the first opening.

The invention also proposes to arrange, on the inside of the cartridge connectors, fixation devices for fixing cartridges in place.

In this context, the invention can provide the fixation devices to be arranged in two concentric rings on the cartridge connectors.

Moreover, it can be advantageous for the fixation devices to be threads, in particular internal threads.

Alternatively, the invention can provide the fixation devices to be snap-in locking devices, in particular in the form of pegs that can be deformed in one direction.

Dispensing devices according to the invention can provide the dispensing device to comprise a trigger grip for operating a valve of the dispensing device, and a base body, in which at least one passage extends that can be closed and opened by the operated valve and through which the pressurised gas can be guided to the cartridge connectors, whereby the opening leads to the passage, whereby the valve is a valve body that is arranged in rotatable manner in the base body, whereby a motion of the trigger grip leads to a rotation of the valve body in the base body, and the passage is arranged in or on the valve body such that the passage is closed in a first position of the valve body, and the passage in or on the valve body guides the pressurised gas to the cartridge connectors in a second position of the valve body.

In this context, the invention can provide at least one front channel to be arranged in the base body between at least one passage and the cartridge connector and/or at least one rear channel to be arranged between at least one passage and the connection for supplying the pressureised gas.

Moreover, the invention can provide a second passage to be arranged in or on the valve body, which connects the cartridge connectors to a first drain in a third position of the valve body such that any over-pressure on the cartridge connectors can escape through the first drain in the third position of the valve body.

In this context, the invention can provide a first drain channel to be arranged in the base body in a manner such that it connects the second passage to the first drain in the third position of the valve body.

Moreover, the invention proposes a third passage to be arranged in or on the valve body, which comprises a branch and connects the cartridge connectors and the pressurised gas to a second drain in the fourth position of the valve body such that an over-pressure in the dispensing device can escape through the second drain in the fourth position of the valve body.

In this context, the invention can provide a second rear channel to be arranged in the base body between the third passage and the connection for supplying the pressurised gas and/or a second drain channel to be arranged in the base body in a manner such that is connects the branch of the third passage to the second drain in the fourth position of the valve body.

The invention can also provide a sterile filter to be arranged on at least one of the drains and/or a pressure relief valve to be arranged in at least one of the drains.

Moreover, dispensing devices according to the invention having rotatable valve bodies can be characterised in that the trigger grip is connected in fixed manner to the underside of the rotatable valve body such that the valve body can be rotated in the base body along with the trigger grip.

Dispensing devices of this type can also be characterised in that a position indicator is arranged on the rotatable valve body, in particular on the top side, on which the position of the valve body in the base body can be detected.

The invention also proposes to arrange on the underside of the dispensing device a handle allowing the dispensing device to be held.

Dispensing devices according to the invention having rotatable valve bodies can also be characterised in that the valve body is a conically-shaped body that is rotationally-symmetrical at least over parts of it, and is mounted in rotatable manner in a conical opening in the base body that matches the shape of the valve body.

In this context, the invention can provide the external walls of the valve body, except for the openings of the passages, to end in a sealed manner against the walls of the conical opening in the base body in any position of the valve body such that the connections of the passages to at least one channel in the base body are sealed.

Moreover, the invention can provide a recess for a wedge in the base body, whereby a wedge that is inserted into the recess presses the valve body into the conical opening in the base body such that the valve body generates a gas-tight press-fit in the conical opening.

Moreover, the invention proposes to provide, on the side of the dispensing device facing away from the cartridge connectors, in particular in the base body, a hollow space for a gas cartridge, whereby the connection for supplying a pressurised gas is arranged in the hollow space and comprises a mandrel for opening a gas cartridge, and fastening means for fastening a closure cap with fastening means is arranged on the base body, whereby the gas cartridge can be opened by the closure cap being fastened, whereby the closure cap preferably comprises an additional locking means that engages a locking device in the hollow space, and whereby it is particularly preferred for the locking device to position an inserted gas cartridge of appropriate size inside the hollow space.

And lastly, the invention proposes the passages to extend essentially straight through the inside of the valve body and the passages to be offset with respect to each other by an angle of 10° to 80° about the rotation axis of the valve body.

The invention is based on the surprising finding that attaching a second cartridge connector around the edge of the first cartridge connector allows a variable cartridge connection to be provided such that the dispensing device not only a small cartridge with just one component as its content, but also a large cartridge system for multiple components, i.e. a large multi-component cartridge, can be attached or fastened to the dispensing device. Through this means, different cartridges or cartridge systems can be squeezed out with the same dispensing device. In the scope of the present invention, a hollow mandrel onto which a cartridge can be pressed to be opened in the process can be a connection for supplying a pressurised gas. A piece of tube with a thread onto which a compressed gas cartridge can be screwed is conceivable as connection just as well. Moreover, a piece of hose that can be plugged onto a connection of a gas cartridge, or a connector on which a hose from a compressor as compressed gas source can be attached also is a connection for supplying a pressurised gas in the scope of the present invention. Even if the compressed gas source is connected to the dispensing device in a fixed manner, for example as part of the base body, the outlet of the compressed gas source into a passage or into a channel in the base body of the dispensing device is a connection for supplying a pressurised gas in the scope of the present invention.

In the scope of the present invention, the front side is the part of the dispensing device that is suitable for insertion of the cartridge. Accordingly, the cartridge is inserted into the cartridge connector from the front. The rear is therefore the opposite part of the dispensing device. The bottom side of the dispensing device is the side that is held downwards in operation.

Sources of pressurised gas can be compressors or cartridges, whereby the cartridges can be filled with a compressed gas, for example a liquefied gas. Carbon dioxide cartridges can be used, for example.

A sterile filter for an outlet can be manufactured from medical paper, gas-permeable plastic membranes, gas-permeable plastic porous discs, gas-permeable metallic porous discs, gas-permeable glass porous discs or gas-permeable plastic fleeces.

The invention also proposes to design the trigger grip to be U-shaped.

The invention can also provide the dispensing device to be essentially made from compatible plastic materials for medical uses.

The invention also proposes the use of a dispensing device of this type for squeezing out flow-able materials from cartridges, whereby the flowable materials are stored in the cartridges, and for squeezing out flowable materials that are stored in bags that are situated in cartridges.

The structure according to the invention very much simplifies the valve function through a rotatable valve body that forms passages together with the base body, or has passages arranged on its inside, in order to be able to implement said functions through inexpensive plastic components. The dispensation of bone cement usually takes in the range of 30 seconds to 5 minutes after the cement is mixed. This means that the valve needs to be able to control a gas flow for just 5 minutes maximally, i.e. the sealing function must be provided for just a few minutes. It can be presumed that the valve is opened and closed no more than five times. Therefore, a simplified valve function of said type is sufficient.

BRIEF DESCRIPTION OF THE DRAWINGS

In the following, exemplary embodiments of the invention are illustrated through seven schematic drawings. In the figures.

DETAILED DESCRIPTION

Figure 1:
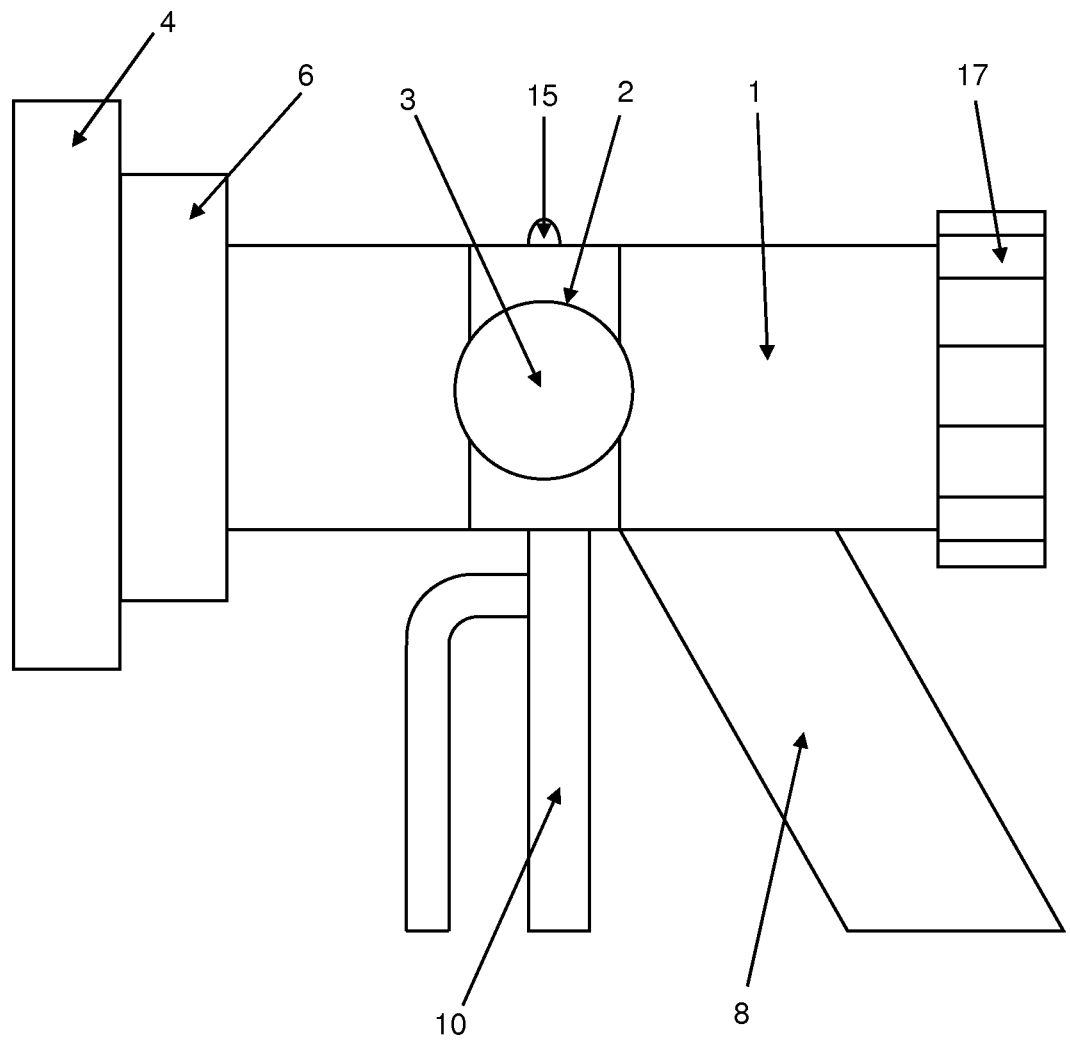
FIG. 1 shows a top view onto the side of a dispensing device according to the invention.

FIG. 1 shows a top view onto the side of a dispensing device according to the invention having a cylinder-shaped base body (1), in which a lateral opening (2) is provided in the form of a bore hole. A valve body (3) having cylindrical geometry is situated in the opening (2) and is mounted such as to be rotatable in the opening (2) and forms a valve together with passages in the valve body (3) and in the base body (1) such that at least two different passages through the valve body (3) and the base body (1) are opened in two different positions of the valve body (3), whereas the other passages are closed. The shape of the valve body (3) is adapted to the shape of the opening (2) in a manner such that the walls of the valve body (3) end in a sealed manner against the opening (2).

A first cartridge connector (4) having a large diameter and a second cartridge connector (6) having a smaller diameter are arranged on the front side (on the left in FIG. 1) of the dispensing device. The two cartridge connectors (4, 6) are shaped as cylindrical hollow bodies that are open on the front side and include walls having openings on the rear side (on the right in FIG. 1). In this context, the single opening of the large cartridge connector (4) is sufficiently large to not cover the internal space of the small cartridge connector (6). The at least two openings in the rear wall of the small cartridge connector (6) lead to the at least two bushings in the base body (1).

A pistol grip (8) is arranged on the underside of the dispensing device (on the bottom in FIG. 1). On the underside of the dispensing device, the valve body (3) is connected to a trigger grip (10), and on the upper side to a position indicator (15), which can be rotated with respect to the base body (1) along with the valve body (3). Labelling (not shown) is provided on the base body (1) that is assigned to the position indicator (15) such that it is feasible to detect which of the passages through the valve body (3) is open at any time, or whether or not the valve is closed. The trigger grip (10) is made up to be U-shaped by two spars such that a user of the dispensing device can easily pull the trigger grip (10) towards the pistol grip (8) or push it away from the pistol grip (8) by finger action between the two spars.

Figure 2:
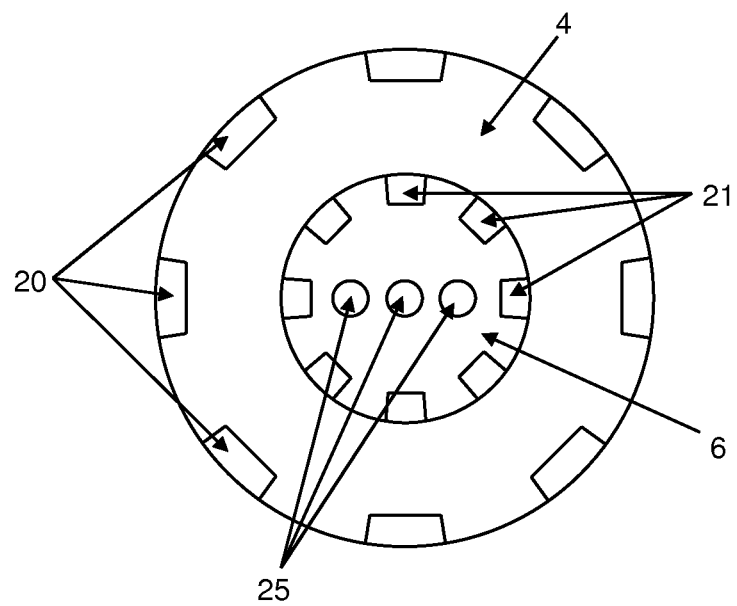
FIG. 2 shows a top view onto the front side of the dispensing device according to the invention according to FIG. 1.

FIG. 2 shows a top view onto the front side of the dispensing device according to the invention according to FIG. 1. The first cartridge connector (4) can be seen as external ring and the second cartridge connector (6) can be seen as internal ring. Fixation devices (20, 21) are arranged in concentric circles on the internal cylinder walls of the cartridge connectors (4, 6) and can be used to fix cartridges (not shown) in place in the cartridge connectors (4, 6). The fixation devices (20, 21) can be implemented through threads, thread sections or pegs for locking the cartridges in the cartridge connectors (4, 6).

Three openings (25) leading to three passages in the base body (1) are situated in the rear wall of the second, inner cartridge connector (6). Cartridges that are fixed in place in the cartridge connectors (4, 6) seal tight against the cartridge connectors (4, 6). This ensures that a gas pressure that is directed through one of the openings (25) to the floor of a fixed cartridge can actually act on said cartridge and does not escape between the cartridges and the cartridge connectors (4, 6). For this purpose, sealing elements (not shown) can be provided in the cartridge connectors (4, 6) and/or on the cartridges, in particular on the cartridge floors. However, it may also be sufficient to provide a sealed fixation device (20, 21) which can be implemented through a thread, for example.

Figure 3:
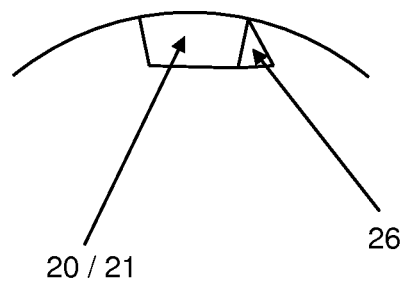
FIG. 3 shows a detailed view of a fixation element according to FIG. 1.

FIG. 3 shows a fixation device (20, 21) according to FIG. 2 that comprises a snap-in locking device (26) that can be used to snap a cartridge in place in a cartridge connector (4, 6). Accordingly, snap-in locking devices (26) in the form of pegs that can be deformed or elastically deformed in one direction can be attached to the fixation devices (20, 21) in order to fix the cartridge in place.

Figure 4:
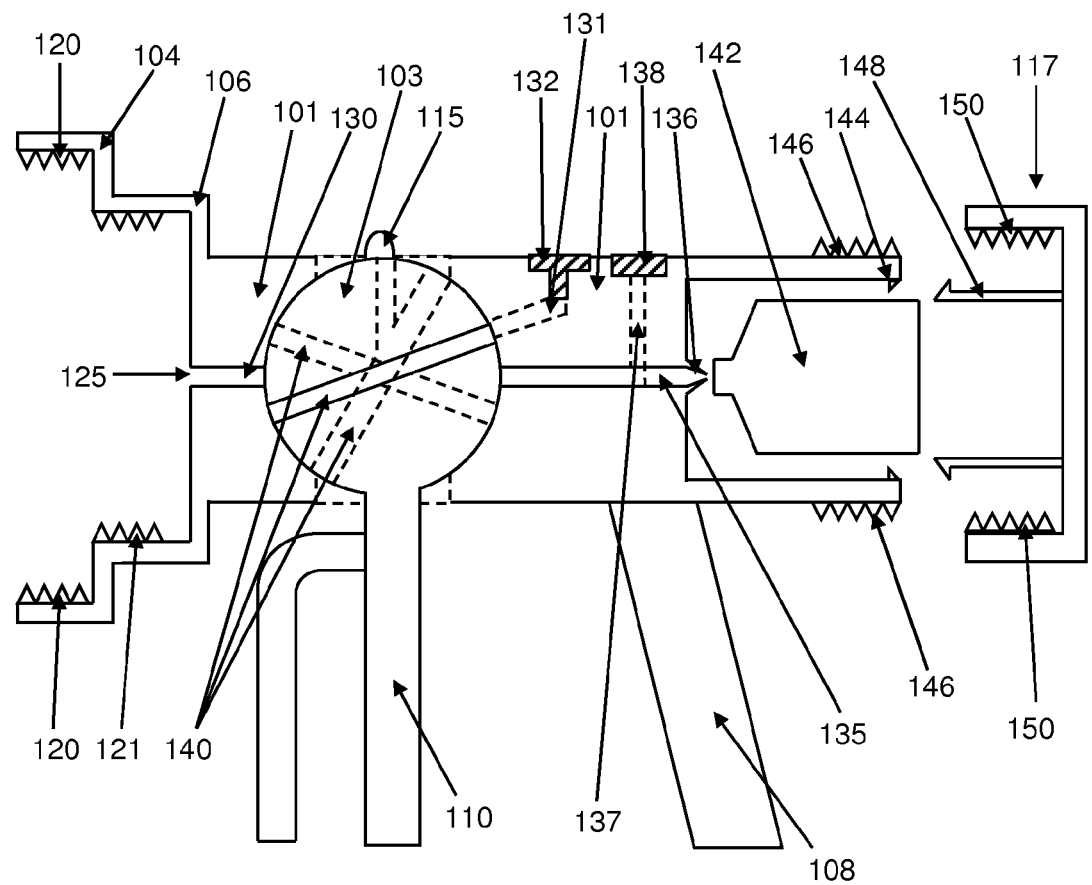
FIG. 4 shows a cross-sectional view of a second dispensing device according to the invention.

FIG. 4 shows a cross-sectional view of a second dispensing device according to the invention having a base body (101) that has a first cartridge connector (104) having a large diameter for cartridges with a large diameter and a second cartridge connector (106) having a smaller diameter for cartridges with a smaller diameter being arranged on its front side. A valve body (103) showing rotationally-symmetrical geometry is situated in an opening (not shown) in the base body (101) and is mounted in the base body (101) such as to be rotatable about its axis of symmetry (perpendicular to the sectional plane shown in FIG. 4).

A pistol grip (108) is arranged on the underside of the dispensing device and allows the dispensing device to be held by one hand. A trigger grip (110) for rotating the valve body (103) in the opening of the base body (101) is arranged on the underside of the valve body (103) and is positioned in front of the pistol grip (108). The trigger grip (110) is designed to be U-shaped such that the fingers of one hand can reach into the intervening space. The arrangement of the trigger grip (110) with respect to the pistol grip (108) is selected in a manner such that the trigger grip (110) can be operated with the fingers of the same hand when the pistol grip (108) is held in one hand. The U-shaped design of the trigger grip (110) permits the valve body (103) to move in both rotational directions.

A position indicator (115) is arranged on the upper side of the valve body (103) and can be used to detect the position of the valve body (103) in the dispensing device. A closure cap (117) can be connected in a detachable manner to the rear side of the base body (101).

Fixation devices (120, 121) in the form of internal threads are provided in the cartridge connectors (104, 106) for fixing in place cartridges having external threads (not shown). A front channel (130) is arranged in the front part of the base body (101) and terminates into an opening (125) towards the cartridge connectors (104, 106) and in a wide opening towards the valve body (103).

Three rear channels (135) terminating in openings towards the valve body (103) are arranged in the rear part of the base body (101). On the side of the base body (101) that faces the rear side of the dispensing device, two of the three rear channels (135) terminate in a hollow mandrel (136) that is open on both sides and has a passage. The third rear channel (135) terminates in a first drain channel (137) that is connected to the surroundings of the dispensing device through a sterile filter (138).

Three passages (140) are arranged in the valve body (103) and are offset along the axis of symmetry of the valve body (103) and, in addition, are twisted with respect to each other about said axis of symmetry. The passages (140) are arranged in the valve body (103) in a manner and the channels (130, 135) are arranged in the base body (101) in a manner such that, in three positions of the valve body (103) that can be adjusted through a rotation of the valve body (103) with respect to the base body (101), the front channel (130) is connected to a rear channel (135) each through one of the passages (140), whereby all other rear channels (135) are closed by the valve body (103). The width of the front opening towards the valve body (103) that terminates in the front channel (130) is sufficient to allow each of the passages (140) to be connected to the front channel (130).

Alternatively, three front channels (130) may be provided in the front part of the base body (101), whereby each front channel (130) can be connected to a rear channel (135) through one passage (140) each. In this case, each of the front channels (130) has a rear channel (135) and a passage (140) assigned to it. Seals (not shown) may be provided about the openings of the channels (130, 135) towards the valve body (103).

One of the three passages (140) connecting the front channels (130) to the rear channels (135) comprises a branch towards a second drain channel (131) that is connected to the surroundings of the dispensing device through a sterile filter (132). A pressure relief valve that opens from a certain pressure can be arranged upstream of the sterile filters (132, 138).

The mandrel (136) projects into a hollow space in the rear part of the base body (101) that is suitable to take up a gas cartridge (142). The purpose of the mandrel (136) is to open a gas cartridge (142) whose opening side is being pressed onto the mandrel (136). On the rear end of the hollow space, a locking device (144) is arranged on the inside, and a fastening means (146) in the form of an external thread is arranged on the outside of the base body (101). The purpose of the locking device (144) is to prevent any inadvertent motion of the closure cap (117). For this purpose, the locking device (144) can engage locking hooks (148) that are arranged on the closure cap (117). The purpose of the fastening means (146) is to connect the closure cap (117) to the base body (101) and, in the process, to push the gas cartridge (142) onto the mandrel (136), and to thus open it. For this purpose, a fastening means (150) is provided on the closure cap (117) in the form of an internal thread.

Figure 5:
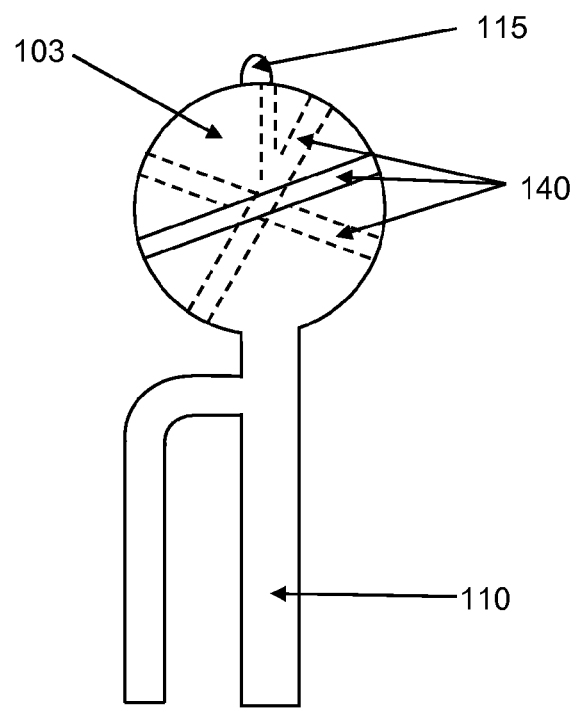
FIG. 5 shows a cross-sectional view of a valve body for a dispensing device according to the invention according to FIG. 4.

FIG. 5 shows a cross-sectional view of the valve body (103) having trigger grip (110) and position indicator (115) according to FIG. 4. Three passages (140), which extend through the valve body (103) at different angles with respect to the trigger grip (110), are situated on the inside of the valve body (103). One of the three passages (140) comprises a branch in the valve body (103) which, in the assembled state, leads to a drain through which the cartridge connectors (104, 106) and an assembled gas cartridge (142) can be ventilated.

Figure 6:
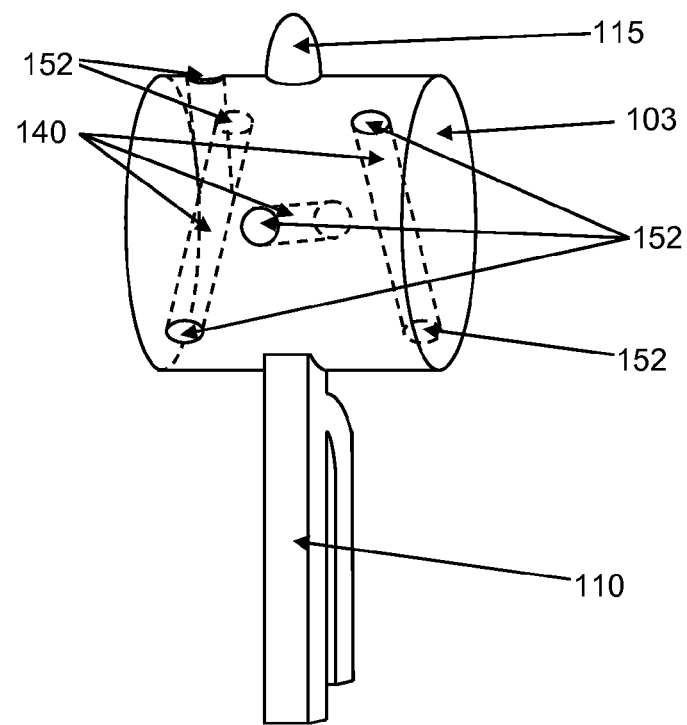
FIG. 6 shows a perspective view of the valve body according to FIG. 5.

FIG. 6 shows a perspective view of the valve body (103) with trigger grip (110) and position indicator (115) according to FIG. 5. Openings (152), into which the three passages (140) terminate, can be seen on the cylinder jacket of the valve body (103). The passages (140) are arranged next to each other and are tilted each by approximately 45° with respect to each other. One of the passages (140) has a branch and thus connects three openings (152).

Figure 7:
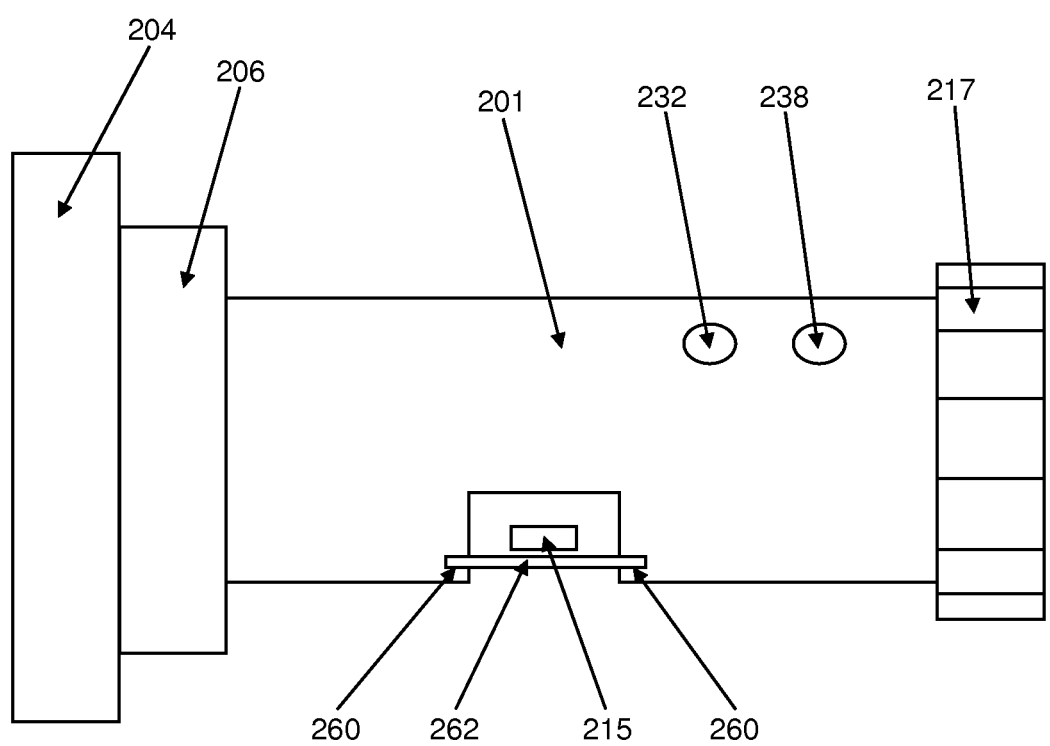
FIG. 7 shows a top view onto the top side of a third dispensing device according to the invention.

FIG. 7 shows a top view onto the top side of a third dispensing device according to the invention comprising a base body (201), on the front side (on the left in FIG. 7) of which two cartridge connectors (204, 206) are connected, namely one cartridge connector (204) with a large diameter for large cartridges and a cartridge connector (206) with a smaller diameter for smaller cartridges. The cartridge connectors (204, 206) comprise a cylinder wall and fastening means (not shown) for fastening the cartridges. Smaller cartridges can be inserted through the interior of the cartridge connector (204) for large cartridges, and can be fastened in the fastening means of the smaller cartridge connector (206).

A closure cap (217) through which a hollow space in the base body (201) for taking up a gas cartridge can be closed is situated on the rear side of the dispensing device (on the right in FIG. 7). Two sterile filters (232, 238) are arranged on the top side of the dispensing device in the region of two openings that are connected to two channels on the inside of the base body (201), whereby the channels permit the hollow space for the gas cartridge, or the gas cartridge itself, to be connected to the cartridge connectors (204, 206).

A conical, rotatable valve body (not shown) is situated on the inside of the base body (201) in a dedicated conical bore hole in the base body (201) that is arranged perpendicular to the connecting line between cartridge connector (206) and closure cap (217), which valve body can be used to connect the various channels between the cartridge connectors (204, 206), the hollow space for the gas cartridge, or the gas cartridge itself, and the openings to the sterile filters (232, 238) and to close them. Passages can be arranged in the valve body for this purpose. The passages may just as well be formed to extend through the external wall of the valve body and the internal wall of the base body (201) in the region, in which the base body (201) and the valve body contact each other. For this purpose, furrows can be provided in the bordering areas between the base body (201) and the valve body, i.e. in the surfaces thereof. A combination of furrows and passages on the inside of the valve body is conceivable as passages of the valve as well.

A position indicator (215) is situated on the top side of the valve body and allows the position of the valve body to be detected and thus to be detected which of the channels is open or whether or not the valve is closed. A recess (260) is provided in the top side of the base body perpendicular to the conical bore hole and serves to take up the valve body and can take up a wedge (262). The recess (260) is arranged in a manner such that the conical valve body is pressed into the conical bore hole when the wedge (262) is being pressed in.

The valve body tapers conically from one side to the other and is fixed in place on the larger side through the wedge (262) being pressed into the base body (201) in the recess (260). By this means, a sufficient contact pressure of the valve body in the bore hole is attained to ensure the desired sealing function. The wedge (262) itself is secured against undesired motions in the direction of the wedge axis through snap-in or locking devices that are common in plastics technology. Alternatively, it is feasible just as well to provide the valve body with at least one external thread and to exert pressure to it, through a screw connection, through at least one nut that is arranged on at least one external side of the base body.

A hollow space for a gas cartridge can be situated on the rear side of dispensing devices according to the invention (on the right in FIGS. 1, 4, and 7) behind the rotatable valve body (3, 103) in the base body (1, 101, 201). For insertion or removal of the gas cartridge, the base body (1, 101, 201) is open towards the rear side of the dispensing device. Said opening can be coverable by a closure cap (17, 117, 217). For this purpose, the closure cap (17, 117, 217) can take the shape of a hollow cylinder that is closed on one side and can be fastened on the base body (1, 101, 201) through fastening means.

The scope of the invention includes that a base body (1, 101, 201) is present, in which at least one bore hole (2) is provided, that one side of the base body (1, 101, 201) is arranged as cartridge connector (4, 104, 204, 6, 106, 206) having at least two fixation devices (20, 120, 21, 121), which are for fixing cartridges in place and form threads or thread sections, that a different side of the base body (1, 101, 201) is provided as pistol grip (8, 108), that a valve body (3, 103) is arranged in the bore hole (2) in a manner such as to be rotatable about its cylinder axis, that the valve body (3, 103) forms a valve made up of a) the valve body (3, 103) having at least two passages (140), b) a position indicator (15, 115, 215), and c) a trigger grip (10, 110), whereby the valve body (3, 103) is connected to the position indicator (15, 115, 215) and the trigger grip (10, 110), that the passages (140) in the valve body (3, 103) are not arranged in the same plane, that at least two front channels (130) are arranged in the base body (1, 101, 201), which form at least two gas-permeable passages between the outside of the cartridge connector (4, 104, 204, 6, 106, 206) and the passages (140), [that] the front channels (130) terminate on the outside of the cartridge connectors (4, 104, 204, 6, 106, 206) in the openings (25, 125) that are situated within the fixation devices (20, 120, 21, 121) for fixing cartridges in place, which are arranged in concentric circles, that at least one drain channel (131) having one of the passages (140) of the valve can be connected to a pressure-sensitive safety valve, which establishes, for a previously set gas pressure, a connection between a front channel (130) and a rear channel (135) and the outside surroundings, that a sterile filter (132) is arranged between the safety valve and the surroundings, that at least one passage (140) of the valve body (3, 103) can communicate with one rear channel (135) that is connected to the gas cartridge (142), that the rear channel (135) can communicate with at least one passage (140) of the valve body (3, 103) and a front channel (130), that a second rear channel (135) having a drain channel (137) connected to it can establish a connection between at least one passage (140) in the valve body (3, 103) and the surroundings, that a sterile filter (138) is arranged between the drain channel (137) and the surroundings, that the second rear channel (135) can be connected through at least one passage (140) in the valve body (3, 103) to a second front channel (130) in a gas-permeable manner.

An advantageous development of the invention can be provided, in addition, in that the gas supplying opening of the gas cartridge (142) is secured through a pin, which can be plugged in and pulled out, or through a plate, which can be unscrewed, in a manner such that the gas cartridge (142) is not pierced to be open prior to application through the action of mechanical forces such as may occur during transport. Moreover, it is feasible just as well to secure the valve body (3, 103) against inadvertent twisting through a pin, which can be pulled out, or a plate. It is particularly advantageous for the securing of the gas cartridge (142) and of the valve body (3, 103) to form a unit and to be removed or inactivated jointly prior to application through, if possible, a single hand motion. The release of the securing of the dispensing device can, for example, be coupled to the gas cartridge (142) being opened.

The base body (1, 101, 201) of the dispensing device and the cartridge connector having two fixation devices (20, 21, 120, 121) arranged in circles, for fixing cartridges in place, and the pistol grip (8, 108) preferably form a unit. Said components are preferably provided as a contiguous unit in the form of an injection moulding component.

Arranging two fixation devices (20, 21, 120, 121) for fixing cartridges in place in two concentric rings is advantageous in that the internal ring can be used to fix in place cartridges having a corresponding small diameter, such as is customary in the case of single cartridges, and in that, if cartridges with a larger diameter are used, for example multi-component cartridges, these can be connected also to the same dispensing device. The advantage being that a dispensing device of this type can be used to squeeze out cartridges of different diameters. This allows the economic efficiency of the dispensing device to be improved.

Aside from arranging fixation devices (20, 21, 120, 121) for fixing cartridges in place in two concentric rings, the scope of the invention also includes providing the fixation devices (20, 21, 120, 121) in rings that are not concentric with respect to each other or, just as well, in non-circular arrangements.

The valve is formed by a valve body (3, 103) that is perforated by at least two passages and has a position indicator (15, 115, 215) and a trigger grip part (10, 110) attached to it. The entire valve including the position indicator (15, 115, 215) and the trigger grip part (10, 110) is preferably a single part and can be manufactured as a single component through injection moulding. Pulling the trigger grip part (10, 110) in the direction of the pistol grip (8, 108), the valve body (3, 103) is rotated in a manner such that the front channels (130) and the rear channels (135) are connected in a gas-permeable manner through the passages (140). With the gas cartridge having been opened earlier, a gas flow then proceeds in the direction of the cartridge connectors (4, 104, 204, 6, 106, 206). The gas flows from the opening (25, 125) and pushes onto the plunger of the cartridge inserted earlier. By this means, the plunger is moved in the direction of the cartridge head and thus squeezes the flowable material out of the cartridge.

Moving the trigger grip part (10, 110) in the direction of the cartridge connector (4, 104, 204, 6, 106, 206), the valve body (3, 103) is rotated in a manner such that the passage (140) no longer connects the continuous front and rear channels (130, 135). In perpendicular position of the trigger grip part (10, 110), the channels (130, 135) are not connected to each other. Rotating the trigger grip part (10, 110) further in the direction of the cartridge connector (4, 104, 204, 6, 106, 206), a passage (140) connects a continuous front channel (130) and the rear channel (135) that is connected to the first drain channel (137). The compressed gas flows from the cartridge connector (4, 104, 204, 6, 106, 206) through one of the openings (125) through one of the continuous front channels (130), through one of the passages (140) and through the first drain channel (137) to the sterile filter (138). The gas exits through the sterile filter (138) into the surroundings. Through this means, compressed gas can be discharged from the space between the cartridge plunger and the cartridge connector (4, 104, 204, 6, 106, 206) via the sterile filter (138) to the surroundings. The motion of the plunger is stopped thereby immediately.

The position indicator (15, 115, 215) projects on the top side of the dispensing device and is automatically moved along upon actuation of the trigger grip part (10, 110), since the position indicator (15, 115, 215) is arranged on the top side of the valve body (3, 103). This means that the position indicator (15, 115, 215) indicates the closure status of the valve. The user is thus kept informed about the closure status of the valve at any time during the use of the dispensing device.

The scope of the invention includes that the passages (140) in the valve body (3, 103) are arranged offset by an angle of at least 10° in a plane that is perpendicular to the axis of the cylinder.

Moreover, the invention can provide front channels (130) and rear channels (135) to be arranged in the base body (1, 101, 201), whereby the first front channel (130) connects the external side of the cartridge connector (4, 104, 204, 6, 106, 206) to a first passage (140) in the valve body (3, 103), whereby the first rear channel (135) connects the first passage (140) to a sterile filter (138) that is connected to the surrounding atmosphere, and provide the valve body (3, 103) to comprise a second passage (140) that connects a second front channel (130) and a second rear channel (135) in a manner such that a gas flow is ensured.

Preferably, the trigger grip part (10, 110) is provided to be U-shaped. This allows the grip part to be pushed in the direction of the cartridge connector through a simple hand motion, and thus allows the flow of gas and thus the flow of the pasty material to be stopped. Moving the trigger grip part (10, 110) further in the direction of the cartridge connector (4, 104, 204, 6, 106, 206) allows the compressed gas to be discharged to the surroundings through a first opening (25, 125) through the first front channel (130), through the first passage (140), through the first rear channel (135), through the drain channel (137), and the sterile filter (138).

The sterile filters (132, 232, 138, 238) can be manufactured from medical paper, gas-permeable plastic membranes, gas-permeable plastic porous discs, gas-permeable metallic porous discs, gas-permeable glass porous discs or gas-permeable plastic fleeces.

The invention can also provide the bore hole (2) in the base body (1, 101, 201) to taper conically from one external side to the other external side and can provide a recess (260) in the base body (1, 101, 201) on the side of the larger opening of the bore hole (2), which recess (260) is perpendicular to the bore hole (2) and can take up a wedge (262). The recess (260) is arranged in a manner such that the valve body (3, 103) is pressed into the bore hole (2) when the wedge (262) is being pressed in.

Specific developments of the present invention can be characterised in that the valve body (3, 103) preferably tapers conically from one side to the other and in that the valve body (3, 103) is fixed in place through a wedge (262) that is pressed into the base body (1, 101, 201) into the recess (260). By this means, sufficient contact pressure of the valve body (3, 103) in the bore hole (2) is attained to ensure the desired sealing function. The wedge (262) itself can be secured against undesired motions in the direction of the wedge axis through snap-in or locking devices that are common in plastics technology. Alternatively, it is feasible just as well to provide the valve body (3, 103) to have at least one external thread on the cylinder end, and to exert pressure on it through at least one nut, through a screw connection, that is arranged on at least one external side of the base body (1, 101, 201).

Preferably, dispensing devices according to the invention are made essentially of compatible plastic materials for medical uses.

Dispensing devices according to the invention are particularly preferably used for squeezing out flowable materials from cartridges, whereby the flowable materials are stored right in the cartridges, and for squeezing out flowable materials that are stored in bags, which in turn are situated in cartridges.

Dispensing devices according to the invention can be used to dispense bone cement, dental materials, adhesives, and sealants from cartridges.

The dispensing device according to the invention can be designed for single and multiple use. Due to the manufacturing costs being low, single use is particularly suitable.

The features of the invention disclosed in the preceding description and in the claims, figures, and exemplary embodiments, can be essential for the implementation of the various embodiments of the invention both alone and in any combination.

In particular, for implementation of the rotatable valve body (3, 103), there is no need to provide more than one cartridge connector (4, 104, 204, 6, 106, 206).

LIST OF REFERENCE NUMBERS 1, 101, 201 Base body
2 Opening
3, 103 Valve body
4, 104, 204 Cartridge connector having a large diameter
6, 106, 206 Cartridge connector having a small diameter
8, 108 Pistol grip
10, 110 Trigger grip
15, 115, 215 Position indicator
17, 117, 217 Closure cap
20, 120 Fixation device
21, 121 Fixation device
25, 125 Opening in the cartridge connector
26 Snap-in locking device
130 Front channel
131, 137 Drain channel
132, 232 Sterile filter
135 Rear channel
136 Hollow mandrel
138, 238 Sterile filter
140 Passage
142 Gas cartridge
144 Locking device
146 Fastening means
148 Locking hook(s)
150 Fastening means
152 Openings in the valve body
260 Recess
262 Wedge

What is claimed:

1. A dispensing device for cartridges comprising a connection for supplying a pressurized gas and a base body, in which at least one passage or a front channel extends through such that the pressurized gas can be guided to a first cartridge connector for connecting a first cartridge, wherein the first cartridge connector comprises a first opening towards the passage or the front channel such that a cartridge content is expellable from the first cartridge through application of the pressurized gas to the first cartridge when the first cartridge is arranged in the first cartridge connector, wherein a second cartridge connector having a larger cross-section and a second opening is arranged at a front edge of the first cartridge connector, wherein the second cartridge connector is suitable for connecting a larger second cartridge, wherein the second opening of the second cartridge connector is sufficiently large to allow the first cartridge to be connected to the first cartridge connector proceeding through the second opening, wherein, on the side of the dispensing device facing away from the cartridge connectors in the base body, a hollow space for a gas cartridge is provided, wherein the connection for supplying a pressurized gas is arranged in the hollow space and comprises a mandrel for opening a gas cartridge and fastening means for fastening a closure cap arranged on the base body, wherein the gas cartridge is openable by the closure cap being fastened, wherein the closure cap comprises a locking means that engages a locking device in the hollow space.

2. The dispensing device according to claim 1, wherein the cartridge connectors are cylindrical hollow bodies having one closed side, wherein the closed side of the second cartridge connector comprises the second opening and the closed side of the first cartridge connector comprises the first opening.

3. The dispensing device according to claim 1, wherein fixation devices, for fixing cartridges in place, are arranged on insides of the cartridge connectors.

4. The dispensing device according to claim 3, wherein the fixation devices are arranged in two concentric circles on the cartridge connectors.

5. The dispensing device according to claim 3, wherein the fixation devices are threads.

6. The dispensing device according to claim 3, wherein the fixation devices comprise snap-in locking devices in the form of pegs that can be deformed in one direction.

7. The dispensing device according to claim 1, wherein the dispensing device comprises a trigger grip for operating a valve of the dispensing device, and the base body, in which at least one passage extends that can be closed and opened by operation of the valve and through which the pressurized gas can be guided to the cartridge connectors, wherein the opening leads to the passage, wherein the valve is a valve body that is arranged in rotatable manner in the base body, wherein a motion of the trigger grip leads to a rotation of the valve body in the base body, and the passage is arranged in or on the valve body such that the passage is closed in a first position of the valve body, and the passage in or on the valve body guides the pressurized gas to the cartridge connectors in a second position of the valve body.

8. The dispensing device according to claim 7, wherein at least one front channel is arranged in the base body between the at least one passage and the cartridge connector and/or at least one rear channel is arranged between at least one passage and the connection for supplying the pressurized gas.

9. The dispensing device according to claim 8, wherein a second passage is arranged in or on the valve body, which connects the cartridge connectors to a first drain channel in a third position of the valve body such that any over-pressure on the cartridge connectors can escape through the first drain channel in the third position of the valve body.

10. The dispensing device according to claim 9, wherein a first drain channel is arranged in the base body in a manner such that it connects the second passage to the first drain channel in the third position of the valve body.

11. The dispensing device according to claim 9, wherein a third passage is arranged in or on the valve body, which third passage comprises a branch and connects the cartridge connectors and the pressurized gas to a second drain channel in a fourth position of the valve body such that an over-pressure in the dispensing device can escape through the second drain channel in the fourth position of the valve body.

12. The dispensing device according to claim 11, wherein a second rear channel is arranged in the base body between the third passage and the connection for supplying the pressurized gas and/or the second drain channel is arranged in the base body in a manner such that it connects the branch of the third passage to the second drain in the fourth position of the valve body.

13. The dispensing device according to claim 12, wherein a sterile filter is arranged on at least one of the drain channels and/or a pressure relief valve is arranged in at least one of the drain channels.

14. The dispensing device according to claim 7, wherein the trigger grip is connected in fixed manner to the underside of the rotatable valve body such that the valve body can be rotated in the base body along with the trigger grip.

15. The dispensing device according to claim 7, wherein a position indicator is arranged on a top side of the rotatable valve body on which the position of the valve body in the base body is detectable.

16. The dispensing device according to claim 1, wherein a handle allowing the dispensing device to be held is arranged on an underside of the dispensing device.

17. The dispensing device according to claim 7, wherein the valve body is mounted in rotatable manner in an opening in the base body that matches a shape of the valve body, wherein external walls of the valve body, except for openings of the passages, end in a sealed manner against the walls of the opening in the base body in any position of the valve body such that connections of the passages to at least one channel in the base body are sealed.

18. The dispensing device according to claim 17, wherein a recess for a wedge is provided in the base body, wherein a wedge that is inserted into the recess presses the valve body into the opening in the base body such that the valve body generates a press-fit in the opening.

19. The dispensing device according to the claim 9, wherein the passages extend essentially straight through the inside of the valve body and the passages are offset with respect to each other by an angle of 10° to 80° about a rotation axis of the valve body.

* * * * *